(12) United States Patent  
Prohens Lopez et al.

(10) Patent No.: US 9,309,201 B2  
(45) Date of Patent: Apr. 12, 2016

(54) PROCESS FOR PREPARATING IVABRADINE HYDROCHLORIDE FORM IV AND METHODS OF TREATMENT OF DISEASE USING IVABRADINE HYDROCHLORIDE FORM IV

(71) Applicant: URQUIMA, S.A., Barcelona (ES)

(72) Inventors: Rafael Prohens Lopez, Barcellona (ES); Cristina Puigjaner Vallet, Barcelona (ES); Rafael Barbas Canero, Barcelona (ES); Jose Luis Del Rio Pericacho, Barcelona (ES); Josep Marti Via, Barcelona (ES)

(73) Assignee: URQUIMA, S.A., Barcelona (ES)

( * ) Notice: Subject to any disclaimer, the term of this patent is extended or adjusted under 35 U.S.C. 154(b) by 0 days.

(21) Appl. No.: 14/806,224

(22) Filed: Jul. 22, 2015

(65) Prior Publication Data

US 2015/0344435 A1    Dec. 3, 2015

Related U.S. Application Data

(63) Continuation of application No. 14/356,240, filed as application No. PCT/EP2012/068615 on Sep. 21, 2012, now Pat. No. 9,139,531.

(30) Foreign Application Priority Data

Nov. 4, 2011    (EP) .................................... 11382339

(51) Int. Cl.
| | | |
|---|---|---|
| *C07D 223/16* | (2006.01) |
| *A61K 9/28* | (2006.01) |
| *A61K 9/20* | (2006.01) |
| *A61K 31/55* | (2006.01) |

(52) U.S. Cl.
CPC ............ *C07D 223/16* (2013.01); *A61K 9/2009* (2013.01); *A61K 9/2013* (2013.01); *A61K 9/2018* (2013.01); *A61K 9/2059* (2013.01); *A61K 9/2095* (2013.01); *A61K 9/284* (2013.01); *A61K 9/2866* (2013.01); *A61K 9/2893* (2013.01); *A61K 31/55* (2013.01)

(58) Field of Classification Search
CPC ...................................................... C07D 223/16
See application file for complete search history.

(56) References Cited

U.S. PATENT DOCUMENTS

2010/0323471 A1    12/2010    Le et al.

FOREIGN PATENT DOCUMENTS

| | | |
|---|---|---|
| CN | 101463008 A | 6/2009 |
| CN | 101597261 A | 12/2009 |
| CN | 101768117 A | 7/2010 |
| CN | 101805289 A | 8/2010 |
| CN | 102050784 A | 5/2011 |
| EP | 0534859 A1 | 3/1993 |
| EP | 1589005 A1 | 10/2005 |
| EP | 1695709 A1 | 8/2006 |
| EP | 1695710 A1 | 8/2006 |
| EP | 1695965 A1 | 8/2006 |
| EP | 1707562 A1 | 10/2006 |
| EP | 1775287 A1 | 4/2007 |
| EP | 1775288 A1 | 4/2007 |
| WO | 2008065681 A2 | 6/2008 |
| WO | 2008125006 A1 | 10/2008 |
| WO | 2008146308 A2 | 12/2008 |
| WO | 2011098582 A2 | 8/2011 |
| WO | 2012025940 A1 | 3/2012 |

*Primary Examiner* — Bruck Kifle
(74) *Attorney, Agent, or Firm* — The Roy Gross Law Firm, LLC; Roy Gross

(57) ABSTRACT

Ivabradine hydrochloride Form IV, its pharmaceutical composition, process for its preparation, and its use as therapeutically active ingredient and pharmaceutical compositions containing Ivabradine hydrochloride Form IV.

17 Claims, 4 Drawing Sheets

PROCESS FOR PREPARATING IVABRADINE HYDROCHLORIDE FORM IV AND METHODS OF TREATMENT OF DISEASE USING IVABRADINE HYDROCHLORIDE FORM IV

FIELD OF THE INVENTION

The present invention relates to ivabradine hydrochloride Form IV, a process for its preparation, its use as therapeutically active ingredient, and pharmaceutical compositions containing it.

BACKGROUND OF THE INVENTION

Ivabradine, (+)-3-[3-[N-[4,5-Dimethoxybenzocyclobutan-1(S)-ylmethyl]-N-methylamino]propyl]-7,8-dimethoxy-2,3,4,5-tetrahydro-1H-3-benzazepin-2-one, is represented by the structural formula (I):

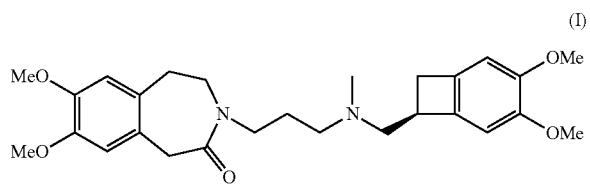 [SMILES: COc1cc2c(cc1OC)CC(=O)N(CCCN(C)C[C@H]1Cc3cc(OC)c(OC)cc31)CC2]

Ivabradine, and addition salts thereof with a pharmaceutically acceptable acid, and more especially its hydrochloride, have very valuable pharmacological and therapeutic properties, especially bradycardic properties, making those compounds useful in the treatment or prevention of various clinical situations of myocardial ischaemia such as angina pectoris, myocardial infarct and associated rhythm disturbances, and also in various pathologies involving rhythm disturbances, especially supraventricular rhythm disturbances, and in heart failure.

Ivabradine is currently marketed with trade name Corlentore and Procolarane for treatment of chronic stable angina pectoris in coronary artery disease patients with normal sinus rhythm.

The preparation and the therapeutic use of ivabradine and addition salts thereof with a pharmaceutically acceptable acid, and more especially its hydrochloride, have been described in the European patent specification EP0534859.

EP0534859 describes a synthesis process for ivabradine and its hydrochloride salt. It is disclosed a product recrystallized in acetonitrile with its melting point Mp: 135-140° C.

EP1589005 discloses the crystalline Form α of ivabradine hydrochloride, characterized by PXRD, and a process for its preparation.

EP1695965 discloses the crystalline Form β, a tetrahydrate form of ivabradine hydrochloride, characterized by PXRD, and a process for its preparation.

EP1695710 discloses the crystalline Form βd of ivabradine hydrochloride, characterized by PXRD, and a process for its preparation.

EP1707562 discloses the crystalline Form γ, a monohydrate form of ivabradine hydrochloride, characterized by PXRD, and a process for its preparation.

EP1695709 discloses the crystalline Form γd of ivabradine hydrochloride, characterized by PXRD, and a process for its preparation.

EP1775288 discloses the crystalline Form δ, a hydrated form of ivabradine hydrochloride, characterized by PXRD, and a process for its preparation.

EP1775287 discloses the crystalline Form δd of ivabradine hydrochloride, characterized by PXRD, and a process for its preparation.

WO2008/125006 discloses a crystalline form of ivabradine hydrochloride, characterized by PXRD, and a process for its preparation.

CN101768117 discloses a crystalline form of ivabradine hydrochloride, characterized by PXRD, and a process for its preparation.

CN101805289 discloses the crystalline Form ω of ivabradine hydrochloride, characterized by PXRD, and a process for its preparation.

WO2011/098582 discloses three crystalline forms of ivabradine hydrochloride, characterized by PXRD, and a process for its preparation.

WO2008/146308, CN101463008, CN101597261 and CN102050784 disclose amorphous form of ivabradine hydrochloride and a process for its preparation.

The polymorphic behaviour of drugs can be of crucial importance in pharmacy and pharmacology. Polymorphism is the ability of a substance to crystallize in different crystal modifications, each of them having the same chemical structure but different arrangements or conformations of the molecules in the crystal lattice. The differences in physical properties exhibited by polymorphs affect pharmaceutical parameters such as storage stability, compressibility and density (important in formulation and product manufacturing), and dissolution rates (an important factor in determining bioavailability). Differences in stability can result from changes in chemical reactivity or mechanical changes or both. For example, a dosage form originating from one polymorph might discolor more rapidly when compound to another from a different polymorph. Or tablets might crumble on storage as a kinetically favoured polymorph spontaneously converts into a thermodynamically more stable polymorphic form. As a result of solubility/dissolution differences, in the extreme case, some polymorphic transitions may result in lack of potency or, at the other extreme, toxicity. In addition, the physical properties of the crystal may be important in processing: for example, one polymorph might be more likely to form solvates or might be difficult to filter and wash free of impurities.

The most important solid state property of a pharmaceutical substance is its rate of dissolution in aqueous fluid. The rate of dissolution of an active ingredient in a patient's gastric fluid may have therapeutic consequences as it imposes an upper limit on the rate at which an orally-administered active ingredient reaches the blood stream. The solid state polymorphic form of a compound may also affect its behaviour on compaction and its storage stability.

These practical physical characteristics are influenced by the conformation and orientation of molecules in the unit cell, which defines a particular polymorphic form of a substance. The polymorphic form may give rise to thermal behaviour different form that of the amorphous material (or) another polymorphic form.

The discovery of new polymorphic forms of a pharmaceutically useful compound provides a new opportunity to improve the performance characteristics of a pharmaceutical product. It enlarges the repertoire of materials that a formulation scientist has for designing, for example, a pharmaceutical dosage form of a drug with a targeted release profile or other desired characteristic.

Usually the most stable polymorphic form is preferred in a marketed formulation, because any other polymorphs are metastable and may therefore transform to the more stable form. Overlooking the most stable polymorph may cause failure of a marketed product due to phase transformation during storage. A late-appearing stable polymorph can have a great impact on development timelines. Although metastable forms may survive years if a considerable activation energy barrier has to be overcome in moving from the metastable state to the stable state, this activation-energy barrier may be reduced by moisture, catalysts, impurities, excipients or temperature and the transformation into the stable form occurs spontaneously. Seeds of the stable form may also accelerate transformations. Therefore using a thermodynamically unstable modification in the production of tablets is sometimes the reason why unwanted changes take place in such formulations after a time of storage. Therefore, there is a need for a thermodynamically stable polymorphic form of ivabradine hydrochloride and methods of its preparation.

A method described by Haleblian and McCrone can be used to determine the most stable polymorph at room temperature. This method utilizes the fact that the most stable polymorph will also be the less soluble at a given temperature and pressure. If crystals of both polymorphs are present in a saturated solution, the most stable form will grow at the expense of the less stable one. This method is called the solution phase transformation or solvent mediated transformation.

Therefore, there is a demand for alternative pure and crystalline forms of ivabradine hydrochloride which would be suitable for use in the pharmaceutical industry and, in particular, allow easy production of ivabradine preparations in solid form meeting strict pharmaceutical standards, such as tablets, capsules, chewable tablets, powders, etc. for oral administration.

To prepare pharmaceutical compositions containing ivabradine hydrochloride Form IV for administration to mammals in accordance with exacting health registration requirements of the U.S. and international health registration authorities, e.g. the FDA's Good Manufacturing Practices ("GMP") requirements, there is a need to produce ivabradine hydrochloride Form IV in as pure a form as possible, especially a form having constant physical properties.

SUMMARY OF THE INVENTION

The applicants have now discovered that the drug substance ivabradine hydrochloride exists in a thermodynamically stable polymorphic form under certain experimental conditions of isolation or purification (ivabradine hydrochloride Form IV). This crystalline form is stable and easy to handle. The improved physical characteristics of said stable crystalline form compared with the ivabradine hydrochloride described in the art, involve enhanced manufacturing capabilities and the provision of a compound suitable for use in the preparation of pharmaceutical formulations.

The applicants have discovered that ivabradine hydrochloride exists as a less thermodynamically stable polymorph or a mixture of polymorphs. Such a mixture could lead to production of a ivabradine hydrochloride Form IV product which would exist as a variable mixture of variable composition (i.e., variable percent amounts of polymorphs) having variable physical properties, a situation unacceptable in view of stringent GMP requirements.

The applicants surprisingly and unexpectedly have obtained a novel thermodynamically stable and pure crystalline form of ivabradine hydrochloride (ivabradine hydrochloride Form IV), having constant physical properties.

Ivabradine hydrochloride Form IV of the present invention is obtained with high yields and elevated richness. Furthermore, the drying conditions used do not affect in the stability of the process, its preparation process is consistently reproducible and robust, and, therefore, easily industrializable. In addition, solvents used during process of obtainment, such as toluene, can be removed without observing changes in the resulting crystalline form (Form IV) or other properties.

Moreover, the applicants have discovered that ivabradine hydrochloride Form IV shows a suitable dissolution profile. The ivabradine hydrochloride Form IV is particularly suitable to obtain immediate release tablets. These tablets can be prepared by known and conventional processes, including direct compression, dry granulation and/or wet granulation. The wet granulation process is performed using organic solvents, acetone or alcohols (such as ethanol, methanol and isopropylalcohol), or the combination thereof.

Furthermore, these tablets can be coated by different conventional excipients. The commonly used coating agents are derivatives of cellulose such as hydroxypropylmethylcellulose (HPMC) and hydroxypropylcellulose (HPC), derivatives of Poly(methyl methacrylate) (PMMA) such as Eudragit®, Polyvinyl alcohol (PVA) and derivates of Polyvinyl alcohol.

Thus, one aspect of the present invention relates to ivabradine hydrochloride Form IV.

In another embodiment, the invention relates to ivabradine hydrochloride Form IV as defined above, with a powder X-ray diffraction comprising the following 2 theta (±0.2) peaks: 8.74, 15.55, 17.17, 19.89, and 24.29, wherein the X-ray diffraction is measured using a CuKα radiation.

In another embodiment, the invention relates to ivabradine hydrochloride Form IV as defined above, with a powder X-ray diffraction comprising the following 2 theta (±0.2) peaks: 8.11, 8.74, 15.55, 17.17, 19.18, 19.89, 21.82, 22.49, 24.29 and 24.53, wherein the X-ray diffraction is measured using a CuKα radiation.

In another embodiment, the invention relates to ivabradine hydrochloride Form IV as defined above, with a powder X-ray diffraction essentially as depicted in FIG. 1.

In another embodiment, the invention relates to ivabradine hydrochloride Form IV as defined above, having a Differential Scanning calorimetry thermogram which shows one endothermic peak from 153° C. to 157° C.

In another embodiment, the invention relates to ivabradine hydrochloride Form IV as defined above, having a Differential Scanning calorimetry thermogram essentially as depicted in FIG. 2.

In another embodiment, the invention relates to ivabradine hydrochloride Form IV as defined above, with an average particle size from 0.1 to 600 μm, preferably from 10 to 100 μm, determined by laser diffraction using Malvern Mastersizer 2000 laser diffraction instrument.

Another aspect of the present invention relates to ivabradine hydrochloric Form, which is essentially the crystalline form disclosed above.

Another aspect of the present invention relates to a process for preparing ivabradine hydrochloride Form IV as defined above, which comprises the step of:
a) slurrying ivabradine hydrochloride in a solvent system, wherein the solvent system comprises toluene, ethanol, acetone, methyl ethyl ketone, methyl isobutyl ketone, ethyl acetate, isopropyl acetate and mixtures thereof.

In another embodiment, the invention relates to the process as defined above, wherein the solvent system comprises at least two solvents.

In another embodiment, the invention relates to the process as defined above, wherein the solvent system comprises toluene and a second solvent selected from ethanol, acetone and ethyl acetate.

In another embodiment, the invention relates to the process as defined above, wherein the temperature of step (a) is lower than 60° C., preferably between 10° C. and 60° C., preferably is lower than 40° C., more preferably from 10° C. to 30° C. and even more preferably from 20° C. to 25° C.

In another embodiment, the invention relates to the process as defined above, wherein the reaction time for performing step (a) is less than 48 h, preferably is less than 24 h.

In another embodiment, the invention relates to the process as defined above, wherein the proportion in step (a) of liter of the solvent system versus kilogram of ivabradine hydrochloride Form IV is from 5 to 50, preferably from 8 to 12.

In another embodiment, the invention relates to the process as defined above, wherein the solvent system in step (a) is essentially toluene.

In another embodiment, the invention relates to the process as defined above, further comprising after performing step (a), the step of:
b) isolating the ivabradine hydrochloride Form IV.

In another embodiment, the invention relates to the process as defined above, further comprising after performing step b, the step of:
c) drying the isolated ivabradine hydrochloride Form IV under vacuum pressure, preferably at a pressure from 25 mm Hg to, but not including, 760 mm Hg, and more preferably from 50 mm Hg to 200 mm Hg, and at a temperature between 45° C. and 70° C.

Another aspect of the present invention relates to a process for preparing ivabradine hydrochloride Form IV as defined above, comprising the steps of:
a) slurrying ivabradine hydrochloride in a solvent system, wherein the solvent system comprises toluene, ethanol, acetone, methyl ethyl ketone, methyl isobutyl ketone, ethyl acetate, isopropyl acetate and mixtures thereof;
b) isolating the ivabradine hydrochloride Form IV, and
c) drying the isolated ivabradine hydrochloride Form IV under vacuum pressure, preferably at a pressure from 25 mm Hg to, but not including, 760 mm Hg, and more preferably from 50 mm Hg to 200 mm Hg, and at a temperature between 45° C. and 70° C.

Another aspect of the present invention relates to a process for preparing ivabradine hydrochloride Form IV as defined above, comprising the steps of:
i) stirring a solution of ivabradine free base in a solvent system, wherein the solvent system comprises toluene, ethanol, acetone, methyl ethyl ketone, methyl isobutyl ketone, ethyl acetate, isopropyl acetate and mixtures thereof;
ii) maintaining the solution at a temperature lower than 60° C., preferably between 10° C. and 60° C., more preferably lower than 40° C.; and more preferably between 10° C. and 40° C.
iii) adding a solution of hydrochloric acid to obtain ivabradine hydrochloride;
iv) seeding with the ivabradine hydrochloride Form IV;
v) isolating the ivabradine hydrochloride Form IV; and
vi) drying the isolated ivabradine hydrochloride Form IV under vacuum pressure, preferably at a pressure from 25 mm Hg to, but not including, 760 mm Hg, and more preferably from 50 mm Hg to 200 mm Hg, and at a temperature between 45° C. and 70° C.

In another embodiment, the invention relates to the process as defined above, wherein the solvent system of step (i), is toluene.

In another embodiment, the invention relates to the process as defined above, wherein the solution of chlorhydric acid of step (iii), is a hydrochloric acid solution in ethanol.

Another aspect of the present invention relates to a process for preparing ivabradine hydrochloride Form IV as defined above, comprising the steps of:
i') stirring a solution of ivabradine free base in a solvent system, wherein the solvent system comprises toluene, ethanol, acetone, methyl ethyl ketone, methyl isobutyl ketone, ethyl acetate, isopropyl acetate and mixtures thereof;
ii') maintaining the solution at a temperature lower than 60° C., preferably between 10° C. and 60° C., more preferably lower than 40° C.; and more preferably between 10° C. and 40° C.
iii') seeding with the ivabradine hydrochloride Form IV;
iv') adding a solution of hydrochloric acid to obtain ivabradine hydrochloride;
v') isolating the ivabradine hydrochloride Form IV; and
vi') drying the isolated ivabradine hydrochloride Form IV under vacuum pressure, preferably at a pressure from 25 mm Hg to, but not including, 760 mm Hg, and more preferably from 50 mm Hg to 200 mm Hg, and at a temperature between 45° C. and 70° C.

In another embodiment, the invention relates to the process as defined above, wherein the solvent system of step (i'), is toluene.

In another embodiment, the invention relates to the process as defined above, wherein the solution of chlorhydric acid of step (iv'), is a hydrochloric acid solution in ethanol.

Another aspect of the present invention relates to a pharmaceutical composition comprising ivabradine hydrochloride Form IV as defined above, and at least a pharmaceutically acceptable excipient.

In another embodiment, the invention relates to the pharmaceutical composition as defined above, for oral administration.

In another embodiment, the invention relates to the pharmaceutical composition as defined above, in the form of tablets.

In another embodiment, the invention relates to the pharmaceutical composition as defined above, in the form of film-coated tablets.

In another embodiment, the invention relates to the coating agents, preferably these agents are derivatives of cellulose, more preferably hydroxypropylmethylcellulose (HPMC) and hydroxypropylcellulose (HPC), derivatives of Poly(methyl methacrylate) (PMMA), more preferably Eudragitt®, Polyvinyl alcohol (PVA) and derivates of Polyvinyl alcohol.

In another embodiment, the invention relates to the pharmaceutical composition as defined above that contains 5 to 9 mg of ivabradine hydrochloride Form IV.

In another embodiment, the invention relates to a film-coated tablet contains about 5 mg ivabradine as free base (equivalent to 5.390 mg ivabradine hydrochloride Form IV).

In another embodiment, the invention relates to a film-coated tablet contains about 7.5 mg ivabradine as free base (equivalent to 8.085 mg ivabradine hydrochloride Form IV).

Another aspect of the present invention relates to a process for the manufacture of the pharmaceutical composition as defined above, characterized in that direct compression, dry granulation and/or wet granulation techniques are used.

Another aspect of the present invention relates to a wet granulation process characterized in that said process comprises using organic solvents, preferably acetone or alcohols (such as ethanol, methanol and isopropylalcohol) or the combination thereof.

Another aspect of the present invention relates to ivabradine hydrochloride Form IV as defined above or the pharmaceutical composition as defined above, for use in therapy.

Another aspect of the present invention relates to ivabradine hydrochloride Form IV as defined above or the pharmaceutical composition as defined above, for use in the treatment of bradycardics, myocardial ischaemia, supraventricular rhythm disturbances, chronic stable angina pectoris in coronary artery disease adults with normal sinus rhythm, myocardial infarct, heart failure and associated rhythm disturbances.

In the above definitions, the term "under vacuum" refers to conditions where the air (gas) pressure surrounding the substrate has been reduced below atmospheric pressure. Preferably under vacuum refers to a pressure from 25 mm Hg to 760 mm Hg (with the proviso that 760 mm Hg is not included), and more preferably from 50 mm Hg to 200 mm Hg.

DETAILED DESCRIPTION OF THE INVENTION

One embodiment of the invention encompasses a thermodynamically stable polymorphic form of ivabradine hydrochloride. This Form may be characterized by X-ray diffraction diagram, measured with a Copper X-ray source, exhibiting characteristic peaks, degrees 2 theta, at about:

| Angle [°2theta] | Relative Intensity [%] |
|---|---|
| 8.11 | 11.59 |
| 8.74 | 9.73 |
| 15.55 | 100.00 |
| 17.17 | 85.38 |
| 19.18 | 78.06 |
| 19.89 | 54.44 |
| 21.82 | 54.91 |
| 22.49 | 64.80 |
| 24.29 | 53.84 |
| 24.53 | 56.00 | and additionally, by one endothermic peak about 155° C. as measured by differential scanning calorimetry (DSC).

The invention also encompasses a process for preparing the claimed crystalline form of ivabradine hydrochloride which comprises the step of slurrying ivabradine hydrochloride in a slurry solvent selected from toluene, ethanol, acetone, methyl ethyl ketone, methyl isobutyl ketone, ethyl acetate, isopropyl acetate and mixtures thereof. Toluene is a preferred slurry solvent and can be used alone or with a second solvent selected from ethanol, acetone and ethyl acetate.

The present invention also discloses a process for preparing the claimed crystalline form of ivabradine hydrochloride which further comprises the step of drying the isolated ivabradine hydrochloride after the slurrying step at a pressure less than 760 mm Hg and the temperature is about 65° C.

Processes for preparing the claimed crystalline form of ivabradine hydrochloride disclosed in the present invention, optionally can include the step of seeding with the novel crystalline form of ivabradine hydrochloride disclosed in the present invention.

Differential scanning calorimetry (DSC) analyses were carried out by means of a Mettler-Toledo DSC-822e calorimeter. Experimental conditions; aluminium crucibles of 40 µL volume, atmosphere of dry nitrogen with 50 mL/min flow rate, heating rate of 10° C./min. The calorimeter was calibrated with indium of 99.99% purity. Instrument could result in a different thermogram. The present invention is characterized by the thermogram values set forth herein obtained using this DSC Instrument as well as the equivalent thermogram values obtained using other types of DSC instruments.

Thermal Gravimetric Analyses (TGA) were performed on a Mettler-Toledo TGA-851e thermobalance. Experimental conditions: alumina crucibles of 70 mL volume, atmosphere of dry nitrogen with 50 mL/min flow rate, heating rate of 10° C./min.

Ivabradine hydrochloride Form IV PXRD analyses: The powder samples were sandwiched between polyester films of 20 micrometers of thickness and analysed in a PANalytical X'Pert PRO MPD θ/θ powder diffractometer of 240 millimeters of radius, in a configuration of convergent beam with a localizing mirror and a flat sample transmission geometry, in the following experimental conditions: Cu K α radiation (I=1.5418 Å); Work power: 45 kV and 40 mA; Incident beam slits defining a beam height of 0.4 millimeters; Incident and diffracted beam 0.02 radians Seller slits; PIXcel detector: Active length=3.347 Å°; 2θ/θ scans from 2 to 40°2θ with a step size of 0.026°2θ and a measuring time of 75 seconds per step.

The term "about" when used in the context of the present invention refers to ±10% of the specified amount. For the purpose of this invention, for X-ray diffraction patterns, depending on the calibration, sample or instrumentation, peaks at 2q can shift up to ±0.2 degrees (error). In one embodiment, all peaks in X-ray diffraction pattern shift up to +0.2 degrees, or up to −0.2 degrees. An X-ray diffraction pattern or peaks within that error is considered the same or substantially similar.

Fourier Transform Infrared—Attenuated Total Reflectance (FT-IR-ATR) spectra were registered on a Perkin Elmer Spectrum One/100 FT-IR spectrometer with universal attenuated total reflectance (ATR) sampling accessory (SPECTRUM100 with UATR1BOUNCE). Sample is placed on the AIR plate and the measure is carried out in the 650-4000 cm-1 range. The term "IR or IR spectrum/spectra" when used in the context refers to spectra registered in the conditions mentioned above.

The term "MiBK" when used in the context of the present invention refers to methyl isobutyl ketone.

The term "MEK" when used in the context of the present invention refers to methyl ethyl ketone.

For the purposes of the invention, any ranges given include both the lower and the upper end-points of the range.

The following drawings and examples illustrate the scope of the invention.

EXAMPLES

Preparative Example 1

Crystalline Ivabradine Hydrochloride

Figure 1:
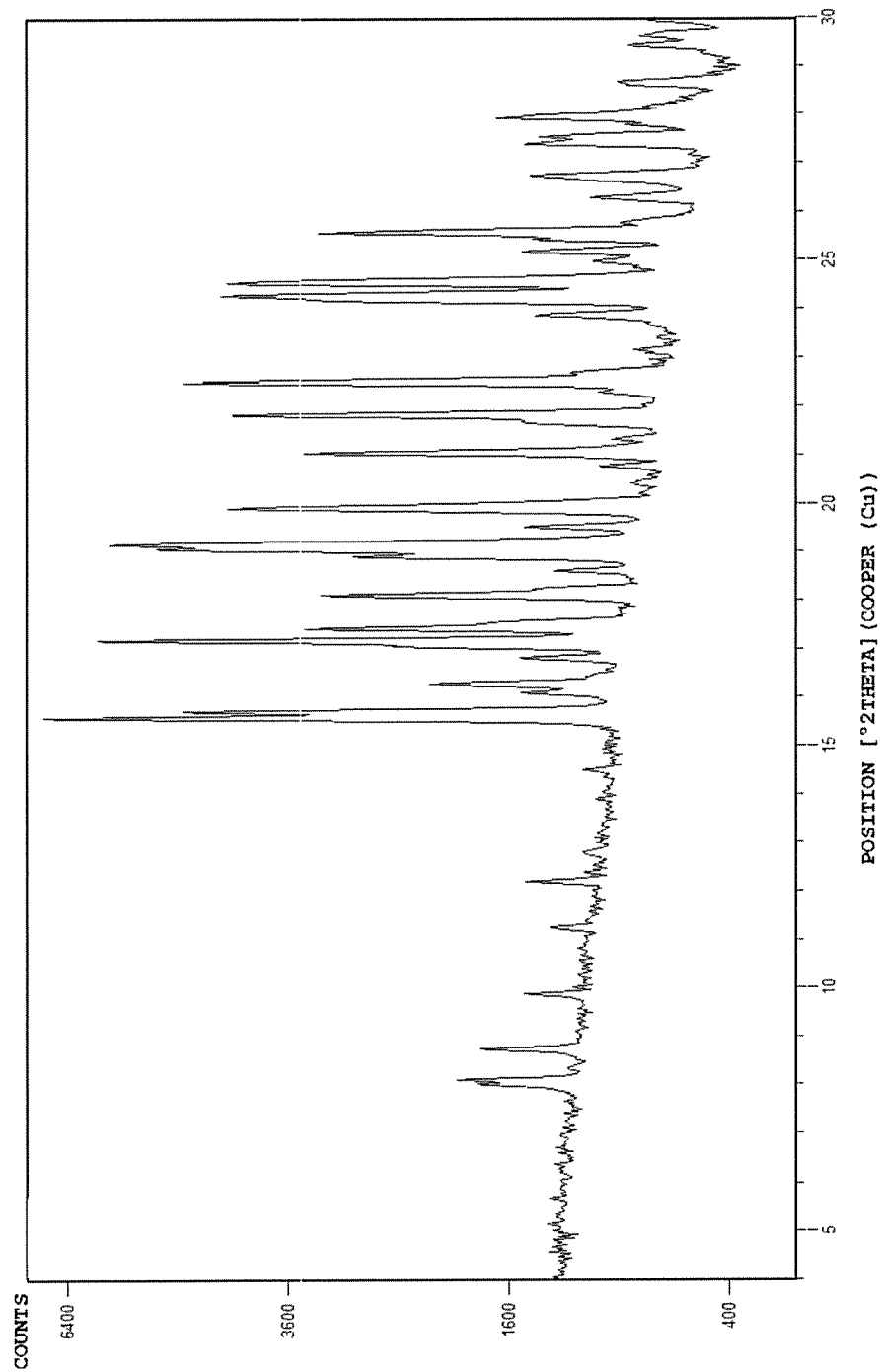
FIG. 1: shows a x-ray diffractogram for the novel crystalline form of ivabradine hydrochloride.
Figure 2:
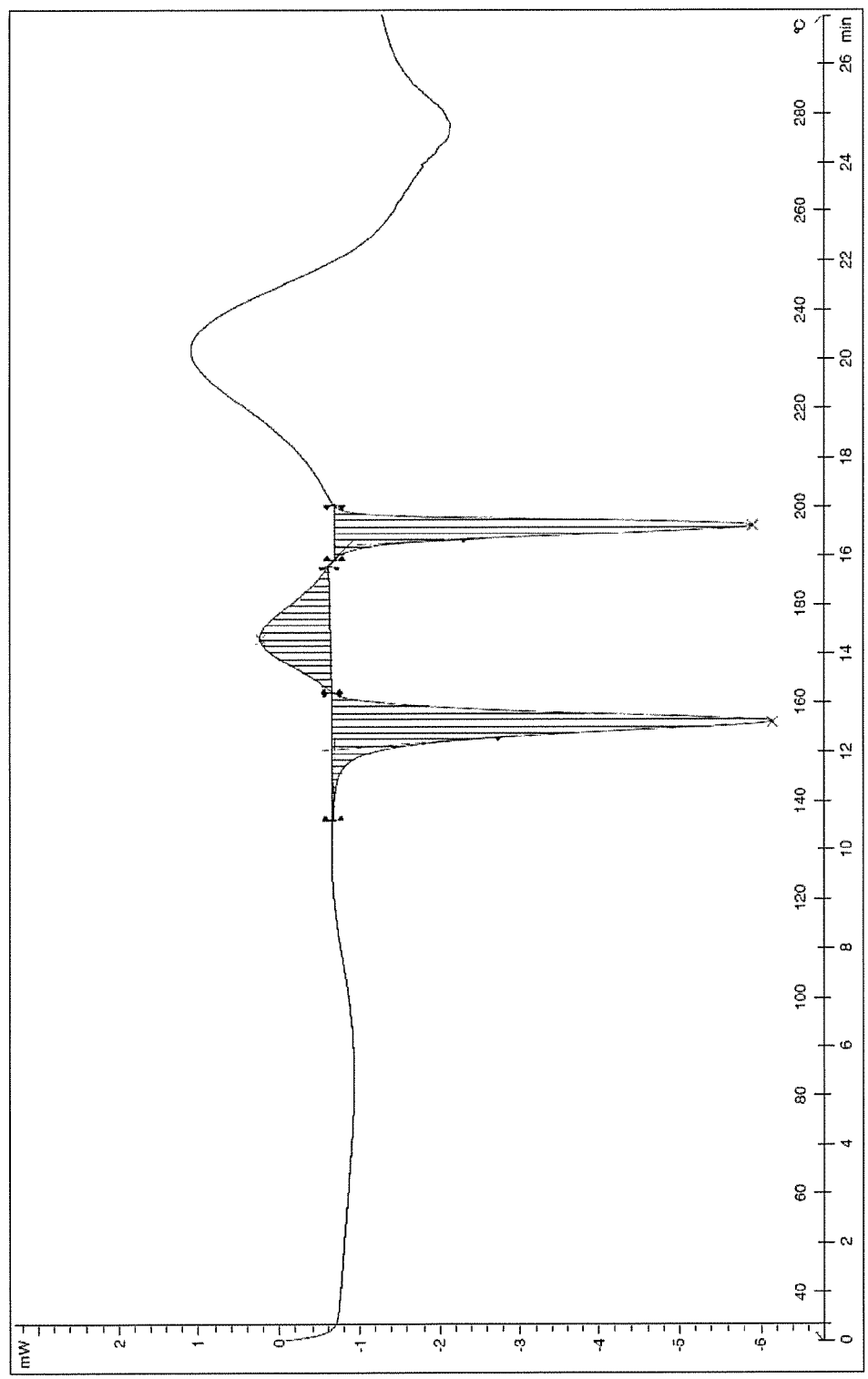
FIG. 2: shows a DSC thermogram for the novel crystalline form of ivabradine hydrochloride.
Figure 3:
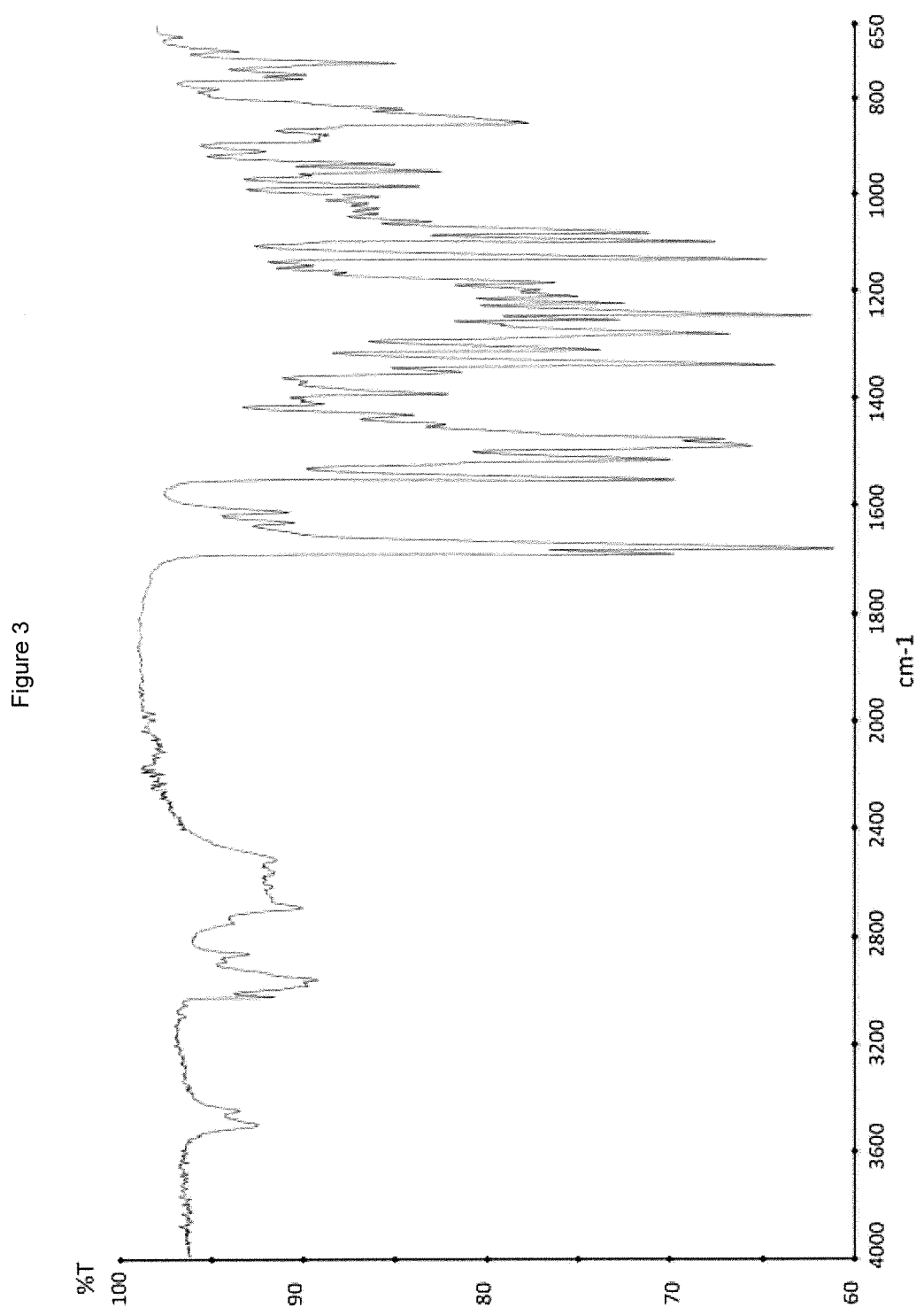
FIG. 3: shows an IR for the novel crystalline form of ivabradine hydrochloride.
Figure 4:
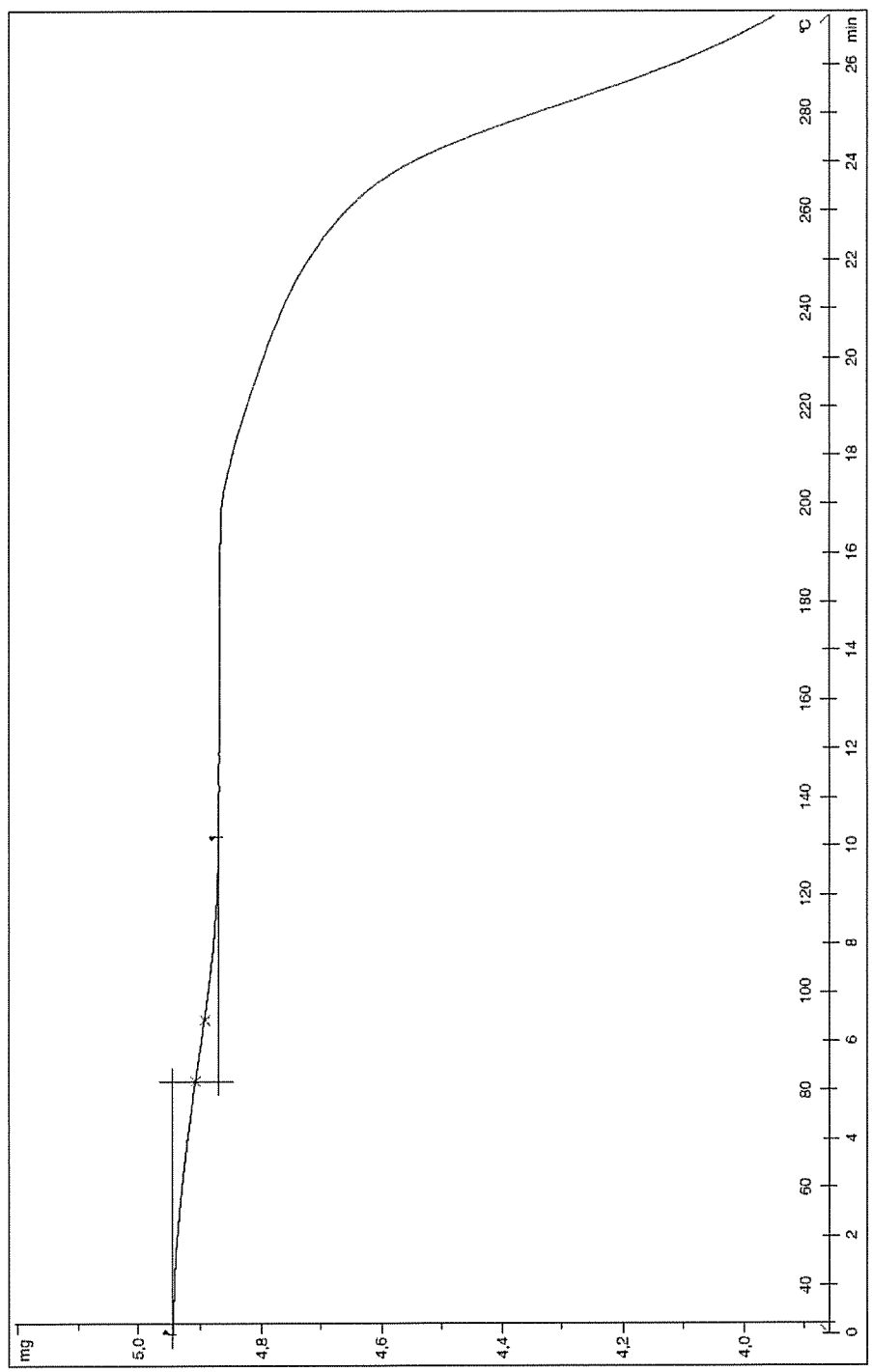
FIG. 4: shows a TGA analysis for the novel crystalline form of ivabradine hydrochloride.

Crystalline ivabradine hydrochloride was obtained according to the process described in the patent EP0534859.

Preparative Example 2

Form α of Ivabradine Hydrochloride

Form α ivabradine hydrochloride was obtained according to the process described in the patent EP1589005.

Preparative Example 3

Form δ of Ivabradine Hydrochloride

Form δ was obtained according to the process described in the patent EP1956005.

Preparative Example 4

Form δd of Ivabradine Hydrochloride

Form δd was obtained according to the process described in the patent EP1775287.

Preparative Example 5

Ivabradine

Ivabradine was obtained according to the process described in the patent EP0534859.

Example 1

Form IV of Ivabradine Hydrochloride 15.0 g of crystalline ivabradine hydrochloride of preparative Example 1 with a Karl Fisher value of 1.6% were slurried with 750 ml of toluene at a temperature of 20-25° C. for 4 days. The solid product was isolated and dried under vacuum at a temperature of 45° C. The crystalline product obtained was characterized by PXRD confirming its structure (HPLC Purity: 99.8%, Yield: 86%).

Examples 2-7

Form IV of Ivabradine Hydrochloride

Examples 2 to 7 were carried out according to the process described in Example 1. In all cases the obtention of Form IV was confirmed by PXRD.

| Example | ivabradine HCl (g) | Solvent (mL) | Yield (%) |
|---|---|---|---|
| 2 | 0.5 | toluene/acetone(10:1) (25) | 91 |
| 3 | 0.5 | toluene/ethyl acetate (10:1) (25) | 87 |
| 4 | 0.5 | ethyl acetate/ethanol (9:1) (5) | 70 |
| 5 | 0.5 | isopropyl acetate (25) | 96 |
| 6 | 0.5 | toluene (5) | 88 |
| 7 | 0.5 | toluene/ethanol (9:1) (5) | 64 |

Example 8

Form IV of Ivabradine Hydrochloride 15.0 g of ivabradine hydrochloride were slurried with 750 ml of toluene at T: 20-25° C. for 1 day. The solid product was isolated and dried under vacuum at a temperature of 45° C. The crystalline product obtained was characterized by PXRD confirming its structure (Yield: 85%).

Example 9

Form IV of Ivabradine Hydrochloride 0.5 g of ivabradine hydrochloride were stirred with 25 ml of ethyl acetate at a temperature of 20-25° C. After seeding with the product obtained in the Example 1 the suspension was slurried for 4 days. The solid product was isolated and dried under vacuum at a temperature of 45° C. The crystalline product obtained was characterized by PXRD confirming its structure (Yield: 88%).

Examples 10-20

Form IV of Ivabradine Hydrochloride

Ivabradine HCl, prepared according to its preparative example, was suspended in the solvent at room temperature. The suspension was slurried at a temperature of 20-25° C. The solid was filtered, dried under vacuum and analysed by PXRD.

| Example | Polymorph | Weight (mg) | Solvent (mL) | Slurry (days) | Result PXRD |
|---|---|---|---|---|---|
| 10 | Form α | 10.0 | MiBK (1.5) | 3 | Form IV |
| 11 | Form α | 10.5 | MiBK (1.5) | 2 | Form IV |
| 12 | Form α | 10.6 | toluene (1.5) | 2 | Form IV |
| 13 | Form α + δd | 10.5 | MEK (1.5) | 2 | Form IV |
| 14 | Form δ | 21.5 | heptane (1.0) | 4 | Form IV |
| 15 | Form δ | 20.6 | MiBK (1.0) | 4 | Form IV |
| 16 | Form δ | 20.0 | toluene (1.0) | 4 | Form IV |
| 17 | Form δ | 20.4 | ethanol/ethyl acetate (1:9) (1.0) | 4 | Form IV |
| 18 | Form δ | 20.5 | ethanol/n-pentane (1:9) (1.0) | 4 | Form IV |
| 19 | Form δd | 20.1 | toluene (1.0) | 4 | Form IV |
| 20 | Form δ + δd | 20.2 | toluene (1.0) | 4 | Form IV |

Example 21

Form IV of Ivabradine Hydrochloride 11.2 mg of ivabradine HCl Form α and 10.0 mg of the Form IV prepared according to Example 1 were suspended in MiBK at room temperature. The suspension was slurried for 3 days at a temperature of 20-25° C. The solid was filtered, dried under vacuum. Analysis by PXRD confirmed that the crystalline ivabradine hydrochloride isolated was in its new crystalline form.

Examples 22-24

Form IV of Ivabradine Hydrochloride

Examples 22 to 24 were carried out according to the process described in Example 21, In all cases the obtention of the novel crystalline form was confirmed by PXRD.

| Example | Form α (mg) | Form IV (mg) | Solvent (mL) | Slurry (days) | Result PXRD |
|---|---|---|---|---|---|
| 22 | 10.6 | 10.5 | MiBK (1.5) | 2 | Form IV |
| 23 | 10.0 | 10.6 | toluene (1.5) | 2 | Form IV |
| 24 | 11.0 | 10.5 | MEK (1.5) | 2 | Form IV |

Example 25

Form IV of Ivabradine Hydrochloride

A solution which comprised 6.9 g of ivabradine in 90 mL of toluene was stirred maintaining the temperature below about 40° C. 16 ml of a chlorhydric acid solution in ethanol 1.75M were added. The solution was seeded with the product obtained in the Example 1. Crystal growth was promoted by stirring for 20 hours maintaining the temperature below about 40° C. The solid product obtained was isolated and dried under vacuum at a temperature of 65° C.

The crystalline product obtained was characterized by PXRD confirming its structure (HPLC Purity: 99.17%, Yield: 68%).

Example 26

Tablets of Form IV of Ivabradine Hydrochloride

Tablets of ivabradine hydrochloride Form IV were prepared using the ingredients listed in the following Table.

| Components | % |
|---|---|
| Ivabradine hydrochloride | 5.39 |
| Maize starch | 15.00 |
| Maltodextrin | 5.00 |
| Silica colloidal anhydrous | 1.00 |
| Monohydrate lactose | 73.11 |
| Magnesium stearate | 0.50 |

All the components, with the exception of magnesium stearate and silica colloidal anhydrous, were mixed. Finally, silica colloidal anhydrous and magnesium stearate were added and mixed. The blend was compressed in an excentric tabletting machine.

The absence of any transformation of the crystalline Form IV of ivabradine hydrochloride was confirmed.

Example 27

Film-Coated Tablets of Form IV of Ivabradine Hydrochloride

Tablets were made with the indicated proportions of the ingredients mention in the following Table.

| Components | % |
|---|---|
| Ivabradine hydrochloride | 5.39 |
| Maize starch | 10.00 |
| Maltodextrin | 10.00 |
| Silica colloidal anhydrous | 1.00 |
| Monohydrate lactose | 72.61 |
| Magnesium stearate | 1.00 |
| Ethanol anhydrous* | — |
| Coating excipient | 3.00 |

*Ethanol evaporates during the drying process

All the components with the exception of magnesium stearate and silica colloidal anhydrous were mixed and granulated using ethanol as a granulating solvent. Then a wet calibration of the granules was performed. The obtained granules were dried followed by a dry calibration of the granules. Thereafter, silica colloidal anhydrous and magnesium stearate were added and mixed. The lubricated granulate was compressed in an eccentric tabletting machine.

Finally, tablets were coated using conventional coating agents until a weight increase of approximately 3%.

The absence of any transformation of the crystalline Form IV of ivabradine hydrochloride was confirmed.

The invention claimed is:

1. A process for preparing ivabradine hydrochloride Form IV with a powder X-ray diffraction comprising the following degrees 2 theta (±0.2) peaks: 8.74, 15.55, 17.17, 19.89, and 24.29, wherein the X-ray diffraction is measured using a CuKα radiation, the process comprising:
   a) slurrying ivabradine hydrochloride in a solvent system comprising toluene, ethanol, acetone, methyl ethyl ketone, methyl isobutyl ketone, ethyl acetate, isopropyl acetate and mixtures thereof; wherein said step of slurrying ivabradine occurs at a temperature of lower than 60° C. and the reaction time for said step of slurrying ivabradine is less than 48 h; and
   b) isolating the ivabradine hydrochloride Form IV.

2. The process of claim 1, wherein the step of slurrying ivabradine occurs at a temperature between 10° C. to 30° C.

3. The process of claim 1, wherein the proportion in step (a) of liter of the solvent system versus kilogram of ivabradine hydrochloride Form IV is from 5 to 50.

4. The process of claim 1, further comprising the step of:
   c) drying the isolated ivabradine hydrochloride Form IV under vacuum pressure and at a temperature between 45° C. and 70° C.

5. The process of claim 1, wherein the solvent system is chosen from toluene and ethyl acetate.

6. The process of claim 1, wherein the process results in a yield % of ivabradine hydrochloride Form IV that is greater than or equal to 64%.

7. A process for preparing ivabradine hydrochloride Form IV with a powder X-ray diffraction comprising the following degrees 2 theta (±0.2) peaks: 8.74, 15.55, 17.17, 19.89, and 24.29, wherein the X-ray diffraction is measured using a CuKα radiation, the process comprising:
   i) stirring a solution of ivabradine free base in a solvent system, wherein the solvent system comprises toluene, ethanol, acetone, methyl ethyl ketone, methyl isobutyl ketone, ethyl acetate, isopropyl acetate and mixtures thereof;
   ii) maintaining the solution at a temperature lower than 60° C.;
   iii) adding a solution of hydrochloric acid to obtain ivabradine hydrochloride;
   iv) seeding with the ivabradine hydrochloride Form IV;

v) isolating the ivabradine hydrochloride Form IV and vi) drying the isolated ivabradine hydrochloride Form IV under vacuum pressure and at a temperature between 45° C. and 70° C.

8. A process for manufacturing a tablet of ivabradine hydrochloride Form IV with a powder X-ray diffraction comprising the following degrees 2 theta (±0.2) peaks: 8.74, 15.55, 17.17, 19.89, and 24.29, wherein the X-ray diffraction is measured using a CuKα radiation, the process comprising:
   a) slurrying ivabradine hydrochloride in a solvent system comprising toluene, ethanol, acetone, methyl ethyl ketone, methyl isobutyl ketone, ethyl acetate, isopropyl acetate and mixtures thereof, and isolating ivabradine hydrochloride Form IV, according to the method of claim 1;
   b) drying the isolated ivabradine hydrochloride Form IV under vacuum pressure and at a temperature between 45° C. and 70° C.;
   c) mixing maize starch, maltodextrin, and monohydrate lactose with ivabradine hydrochloride Form IV;
   d) adding magnesium stearate and anhydrous colloidal silica to the mixture of step d); and
   e) compressing the mixture of step e) in a tableting machine to form one or more tablets of ivabradine hydrochloride Form IV.

9. The process of claim 8, further comprising coating the one or more tablets of ivabradine hydrochloride Form IV using a coating excipient.

10. The process of claim 9, wherein the coating excipient is selected from a group consisting of derivatives of cellulose, more preferably hydroxypropylmethylcellulose (HPMC) and hydroxypropylcellulose (HPC), derivatives of Poly(methyl methacrylate) (PMMA), more preferably Eudragit®, Polyvinyl alcohol (PVA) and derivates of Polyvinyl alcohol.

11. A method for the treatment of chronic stable angina pectoris in an adult with normal sinus rhythm, the method comprising administering an effective amount of ivabradine hydrochloride Form IV with a powder X-ray diffraction comprising the following degrees 2 theta (±0.2) peaks: 8.74, 15.55, 17.17, 19.89, and 24.29, wherein the X-ray diffraction is measured using a CuKα radiation.

12. The method of claim 11, further comprising administering at least a pharmaceutically acceptable excipient with said effective amount of ivabradine hydrochloride Form IV to said adult.

13. The method of claim 11, wherein the effective amount of ivabradine hydrochloride Form IV is administered via a tablet.

14. The method of claim 13, wherein the tablet includes 5 mg to 9 mg ivabradine hydrochloride Form IV.

15. The method of claim 13, wherein the tablet is administered via oral administration.

16. A method for the treatment of chronic stable angina pectoris in coronary artery disease adults with normal sinus rhythm comprising administering to said adult an effective amount of ivabradine hydrochloride Form IV with a powder X-ray diffraction comprising the following degrees 2 theta (±0.2) peaks: 8.74, 15.55, 17.17, 19.89, and 24.29, wherein the X-ray diffraction is measured using a CuKα radiation.

17. The method of claim 16, further comprising administering at least a pharmaceutically acceptable excipient with said effective amount of ivabradine hydrochloride Form IV to said adult.

* * * * *